(12) United States Patent
Brunnberg et al.

(10) Patent No.: US 6,880,555 B1
(45) Date of Patent: Apr. 19, 2005

(54) INHALER

(75) Inventors: Lennart Brunnberg, Tyreso (SE); Thomas Olsson, Stockholm (SE)

(73) Assignee: SHL Medical AB, Nacka (SE)

( * ) Notice: Subject to any disclaimer, the term of this patent is extended or adjusted under 35 U.S.C. 154(b) by 220 days.

(21) Appl. No.: 10/110,375

(22) PCT Filed: Oct. 12, 2000

(86) PCT No.: PCT/SE00/01976

§ 371 (c)(1),
(2), (4) Date: Jul. 12, 2002

(87) PCT Pub. No.: WO01/26720

PCT Pub. Date: Apr. 19, 2001

(30) Foreign Application Priority Data

Oct. 12, 1999 (SE) .............................................. 9903677
Jan. 13, 2000 (SE) .............................................. 0000092

(51) Int. Cl.[7] ........................................... A61M 15/00
(52) U.S. Cl. ............................ 128/203.12; 128/203.15; 128/203.21
(58) Field of Search ....................... 128/203.12, 203.15, 128/203.21, 205.21; 604/58

(56) References Cited

U.S. PATENT DOCUMENTS

| | | | | |
|---|---|---|---|---|
| 3,127,058 A | * | 3/1964 | Johnston | 222/5 |
| 3,967,761 A | * | 7/1976 | Melton et al. | 222/635 |
| 5,349,947 A | * | 9/1994 | Newhouse et al. | 128/203.21 |
| 5,488,946 A | * | 2/1996 | Calhoun et al. | 128/205.21 |
| 5,495,083 A | * | 2/1996 | Aymami-Pala et al. | 218/1 |
| 5,533,502 A | * | 7/1996 | Piper | 128/203.21 |
| 5,692,496 A | * | 12/1997 | Casper et al. | 128/203.15 |
| 5,694,920 A | * | 12/1997 | Abrams et al. | 128/200.16 |
| 5,715,810 A | * | 2/1998 | Armstrong et al. | 128/203.15 |
| 5,740,794 A | * | 4/1998 | Smith et al. | 128/203.15 |
| 5,769,073 A | * | 6/1998 | Eason et al. | 128/203.15 |
| 5,785,049 A | * | 7/1998 | Smith et al. | 128/203.15 |
| 5,823,183 A | * | 10/1998 | Casper et al. | 128/203.15 |
| 5,988,163 A | * | 11/1999 | Casper et al. | 128/203.15 |
| 6,089,228 A | * | 7/2000 | Smith et al. | 128/203.15 |
| 6,116,239 A | * | 9/2000 | Volgyesi | 128/203.15 |
| 6,257,233 B1 | * | 7/2001 | Burr et al. | 128/203.15 |
| 6,520,179 B1 | * | 2/2003 | Von Schuckmann et al. | 128/203.15 |
| 6,543,448 B1 | * | 4/2003 | Smith et al. | 128/203.15 |
| 6,546,929 B1 | * | 4/2003 | Burr et al. | 128/203.15 |
| 6,604,522 B1 | * | 8/2003 | Arvidsson et al. | 128/203.15 |
| 6,668,827 B1 | * | 12/2003 | Schuler et al. | 128/203.21 |
| 6,679,256 B1 | * | 1/2004 | Ingle et al. | 128/203.21 |
| 6,722,363 B1 | * | 4/2004 | Von Schuckmann | 128/203.15 |

FOREIGN PATENT DOCUMENTS

| | | |
|---|---|---|
| EP | 0 129 985 A1 | 1/1985 |
| EP | 0 525 720 A1 | 2/1993 |
| WO | 90/13328 | 11/1990 |
| WO | 95/06491 | 3/1995 |

* cited by examiner

*Primary Examiner*—Aaron J. Lewis
(74) *Attorney, Agent, or Firm*—Young & Thompson

(57) ABSTRACT

An inhaler for medicament in powder form with an opening intended for inhalation. The powder medicament is arranged in the inhaler in a number of enclosures, each enclosure including a specific dose of medicament. A member is provided for enabling access to the dose of medicament. The member is arranged and designed such that it is able to be inserted inside the enclosure and establish at least one outlet passage, between the interior of the enclosure and the inhalation opening, through which outlet passage the medicament is delivered to the patient upon inhalation.

14 Claims, 13 Drawing Sheets

INHALER

TECHNICAL FIELD

Figure 1:
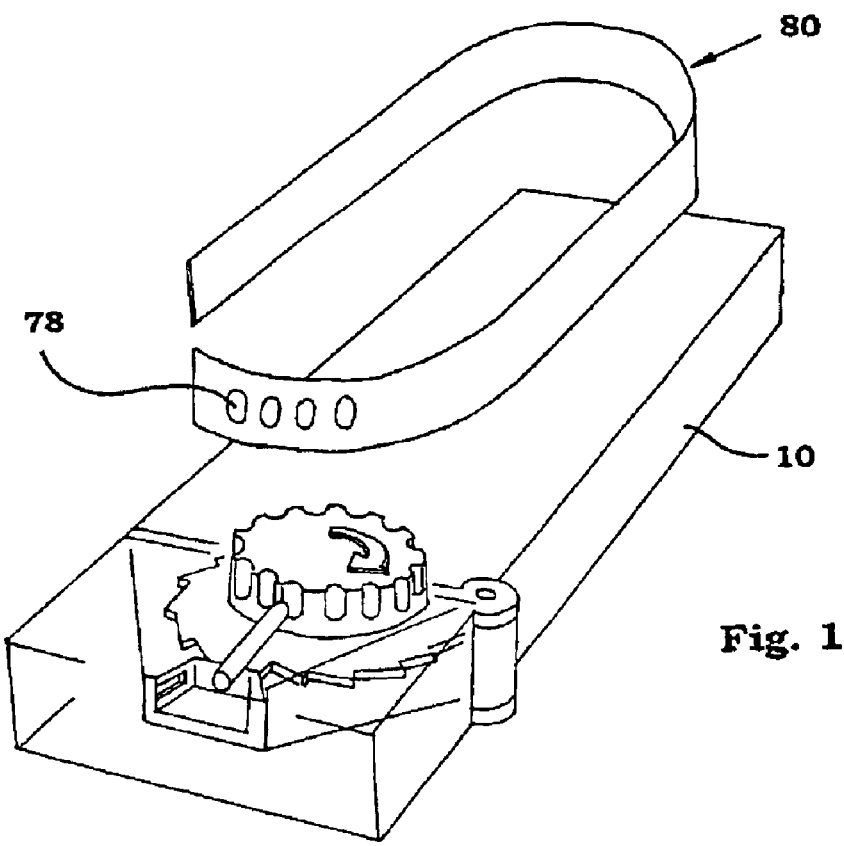

The present invention relates to an inhaler for medicament in powder form with an opening intended for inhalation. The powder medicament is arranged in the inhaler in a number of enclosures, where each enclosure comprises a specific dose of medicament.

BACKGROUND OF THE INVENTION

Inhalers for delivering medicaments into the respiratory tract are widely used and there are three major forms of inhalers for delivering the medicament, aerosol-driven and nebulizers, with the medicament in some kind of liquid form, and powder, each with its advantages and drawbacks.

Inhalers for medicament in powder form, hereafter named powder inhalers, are provided with a compartment for containing the medicament, devices for extracting a dose from the compartment and placing it in, or close by, an air passage communicating with an opening and/or mouthpiece for inhalation. In some types of powder inhalers, the compartment is rather large, containing a large number of doses in bulk form. These are then provided with feeding means for extracting one dose which is placed so that the inhalation air flow carries the dose. One major drawback with these is that many powders are sensitive to moist and humidity. If moist enters the compartment, it binds the powder, thereby forming larger pieces of medicament, above sizes suitable for inhalation into the respiratory tract. This sensitivity to humidity has in practice limited the use of powder inhalers in such areas in the world where air humidity is high.

One way of protecting the powder and to facilitate the dosage is to package the powder so that each package contains one dose and that the package is opened when the medicament is to be delivered. One such device utilises two strips joined together with dose compartments in between. As one dose is to be delivered, the strips are separated so that the dose is exposed. The dose falls down on a tray or the like arranged in the air passage so that, upon inhalation the dose is delivered to the patient. The rest of the doses remain protected from moist by the strips.

A problem with that type of inhaler is that the dose is not held or protected by anything once it has fallen on the tray. If the patient then tilts or in any way moves or shakes the inhaler, or exhales through the device, before inhalation the powder will most likely fall or be blown off the tray and disappear, into the inhaler mechanism and possibly disrupt the function, or from the inhaler to a large extent. The patient will then upon inhalation not receive an adequate dose.

Another problem with many powder inhalers is the relative long passage ways between the delivery point and the inhalation opening. Since the powder does not follow the air flow in a linear manner, but rather turbulent, powder is deposited on the internal walls of the inhaler, thus causing a build-up of powder in certain areas. This means also that the patient does not receive a full dose of medicament. These "collections" of powder may eventually loosen upon inhalation whereby the patient may receive an over-dose of medicament. Generally speaking, the deposition of powder may lead to a variation in the doses delivered.

Other powder inhalers utilise capsules containing specific doses of medicament where the capsules protect the medicament. The capsules are placed in an inhaler, and when a patient is to take a dose, means are arranged to open the capsule so that the medicament is carried by an air flow through the capsule upon inhalation. Frequently these capsules are cut or slit open by knives, needles or the like. Upon cutting the capsule, there is a risk that pieces from the capsule are cut off or that pieces are torn off during inhalation. These pieces may then get stuck in the air passage of the inhaler and disturb its function, or worse, be drawn into the respiratory tract of the patient.

For all powder inhalers, there is a general belief that in order to aerolise the powder and deliver the whole dose the inhalation of the patient should be strong initially in order to obtain the above criteria but also in order for the powder to reach into the lower parts of the respiratory tract.

One problem is that a more or less continuous air flow through the compartment containing the dose of medicament does not ensure a proper aerolisation and complete emptying of the compartment even though the air flow may be stronger initially. Further, recent research has shown indications that it may not be the initial amount of air inhaled that reaches the lowest parts of the respiratory tract but rather subsequent air. For some types of medicament which are most effective if they reach the lower respiratory tract, doses might not optimally reach those areas with the conventional inhalers. Further indications show that slow inhalations, as low as e.g. 10 l/min or even lower might be advantageous and preferable with certain types of drugs and/or particle sizes to inhale into the respiratory tract.

BRIEF DESCRIPTION OF THE INVENTION

The aim of the present invention is to provide an inhaler for powder medicament without the above mentioned drawbacks, which is easy and reliable in use, delivers an adequate dose of medicament upon proper inhalation with a high dose to dose equivalence, and between use, protects the powder from moist and the like conditions.

This aim is achieved according to one aspect of the invention with an inhaler according to the preamble of the description characterised in means for enabling access to said dose of medicament, wherein said means is arranged and designed such that it is able to be inserted inside said enclosure and establish at least one passage between the interior of said enclosure and said inhalation opening, through which passage the medicament is delivered to the patient upon inhalation.

According to another aspect of the invention it is characterised in that it comprises at least one further passage, which further passage, upon inhalation, acts as an air supply to the enclosure.

According to a further aspect of the invention it is characterised in that said pointed end (-s) has a shape in the form of a number of side walls, where each side wall has the shape of a triangle, that one corner of each triangle together form a pointed end, that the edges of adjacent triangles act as cutters when breaking through the enclosure wall, and that the opening of the passage (-es) is arranged in at least one of the side walls.

According to yet an aspect of the invention, it is characterised in that said means for enabling access is activated when the pressure drop/air flow in an air passage in said inhaler reaches a certain threshold value.

According to a further aspect of the invention, it is characterised in that the distance between the dose enclosure and the inhalation opening is as short as possible thus minimising drug contacting surfaces, and that an air ejector means is arranged adjacent said air opening in communication with said dose access enabling means.

The advantages with the invention as compared to the state of the art are several. Because the medicament is packaged in doses, it is very convenient to handle by the device and since the means for enabling access to the medicament is inserted into the dose enclosure, the risk of medicament disappearing, falling off the delivery tray or getting lost in the device or outside by accidental or unintended improper handling of the device after the medicament is exposed, is substantially avoided.

Because the dose enclosure is opened preferably by elongated bodies with pointed ends, providing passages for the medicament to the inhalation opening, and because the bodies are inserted into the enclosure on start of inhalation and stationed there during the inhalation, the medicament can only escape through these passages and is exposed to the surrounding atmosphere to a minimised extent.

Since the pointed ends preferably are arranged by triangular side walls where one corner of each triangle together form the end point and that the edges of the triangles act as cutters, a very controlled opening of the enclosure is obtained. Since the side walls are substantially flat the enclosure wall will roll up along the side walls and form a kind of seal, preventing the medicament from escaping there through.

Preferably the means for enabling access is activated upon inhalation. Due to this, the enclosure is opened by inserting the means inside the enclosure only when a patient inhales in the device. Thus the medicament is only exposed for a very short moment and between inhalation the subsequent doses of medicament are safely stored inside the dose enclosures. This feature further ensures that no medicament will be lost due to improper handling of the device. This feature also provides for inhalation regardless of position of the inhaler, thus enabling inhalation when lying down.

Preferably the means for enabling access is arranged with at least two passages, one in communication with the inhalation opening and the other in communication with the interior of the inhaler, preferably in the vicinity of the dose activation means. This ensures a flow of air through the enclosure, which air flow transports the medicament in powder form.

Preferably the passage ways between the dose enclosure and the inhalation opening are short in order to minimise the risk of powder depositing on the interior of the device.

The inhaler is further preferably arranged with an ejector means arranged in the air passage adjacent the end of the medicament passage opposite the end arranged inside the enclosure, to increase the flow through the enclosure, thus ensuring a proper emptying of the enclosure during inhalation. This is especially important with very small doses of medicament in rather small enclosures. Because of the size of the enclosures, the passages by necessity need to be small. In order to be able to properly aerolize the medicament and deliver it through the passage(-s), a sufficient air flow has to be created, which is ensured according to the present invention with the ejector means. With the small passages, the total inhalation air flow can not be directed through these. A part of the air flow has to be taken from, and directed through the air passage, which air flow, when passing the ejector means, creates and increases the air flow through the passages.

Also a swirling effect, which is obtained according to the present invention by directing the openings of the inlet and outlet passages in different directions and/or the configuration of the enclosures, aid in proper emptying of the enclosures.

The aim of the present invention is further to provide a device for a powder inhaler that ensures a proper aerolisation and emptying of the powder compartment and also no longer necessitates a strong initial inhalation and/or subsequent strong inhalation flow.

This aim is obtained according to one aspect of the invention with a device according to the preamble of the description characterised in an air supply means capable of, during inhalation, supply air via the inlet passage to the compartment intermittently.

According to another aspect of the invention, it is characterised in that the air supply means is capable of generating and supplying intermittent air flow with an increased pressure.

According to a further aspect of the invention, it is characterised in that the inhaler is arranged with a third air passage, hereafter named outer passage, connected to the inhalation opening, in that the outlet end of the outlet passage is arranged in the outer passage, and in that adjacent the outlet end, the inhalation opening is arranged with inhalation air balancing means. With low air flows, the inhalation air balancing means acts a kind of throttle of the outer passage thereby balancing the amount of the inhalation air between the outer passage and the outlet passage, controlling the amount of air/medicament in the outlet passage. With higher air flows it provides a kind of ejector effect whereby the flow of air/medicament in the outlet passage is promoted.

The present invention displays a number of advantages in relation to the state of the art.

Figure 2:
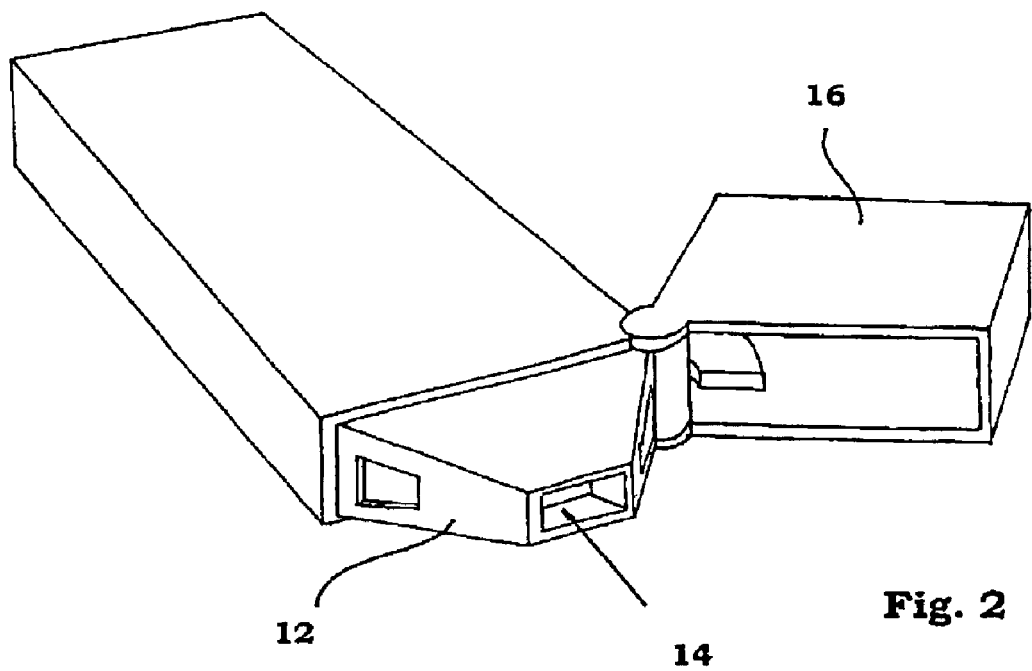
Figure 3:
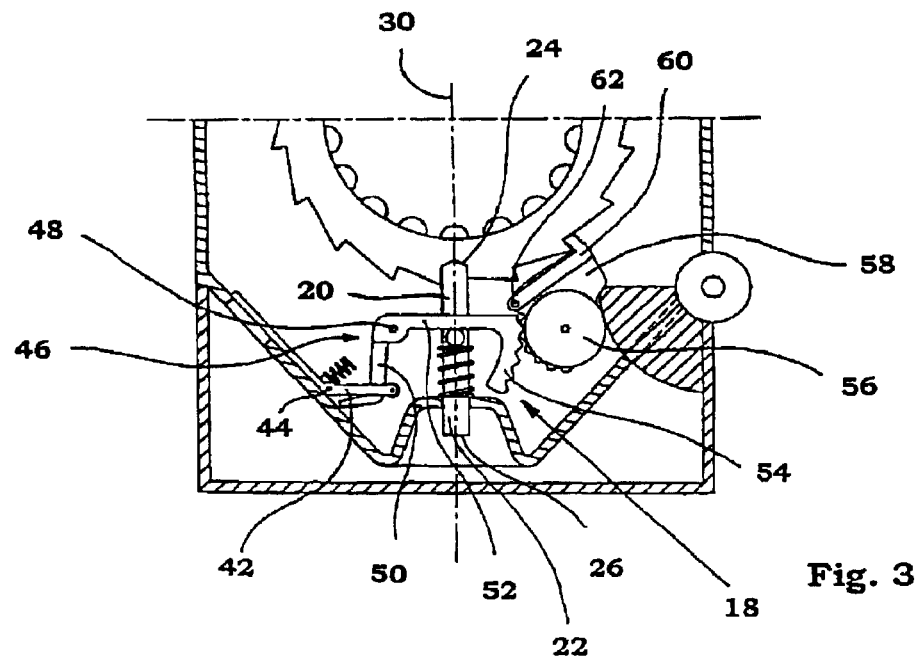
Figure 4:
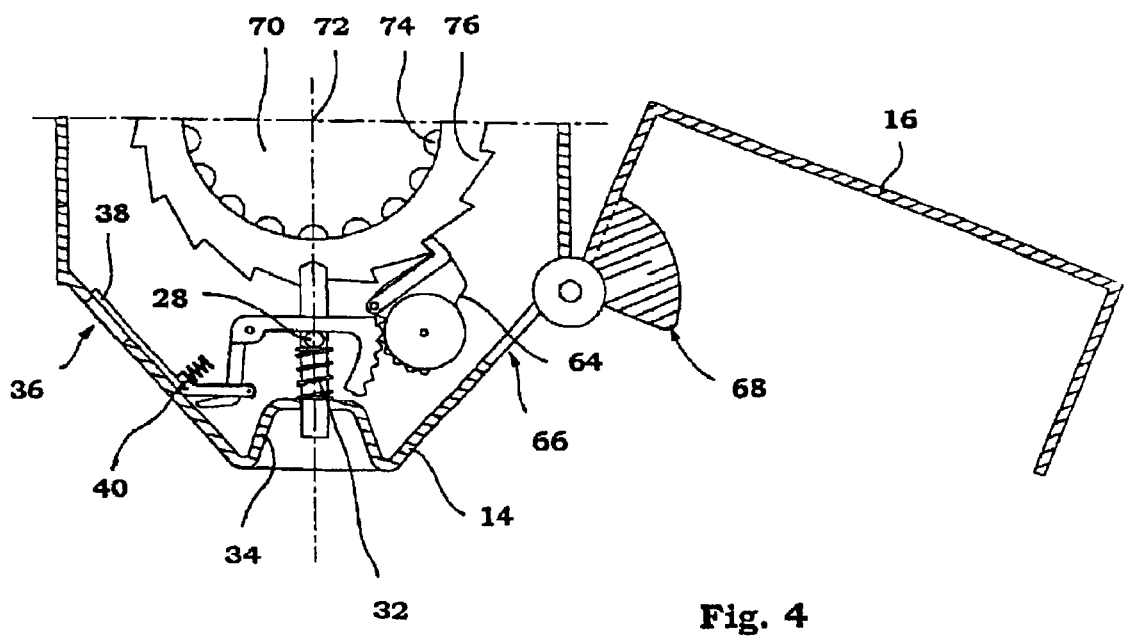
Figure 5:
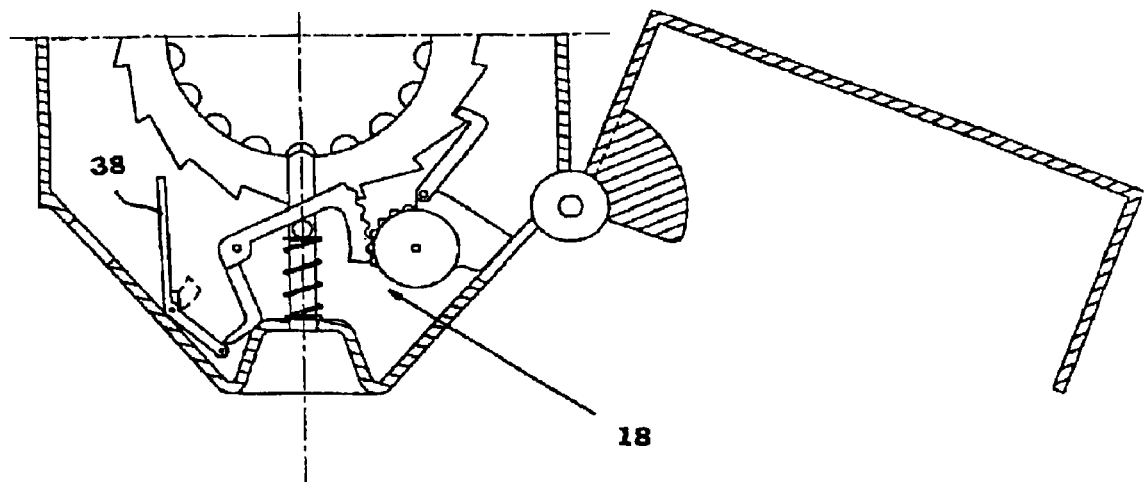
Figure 6:
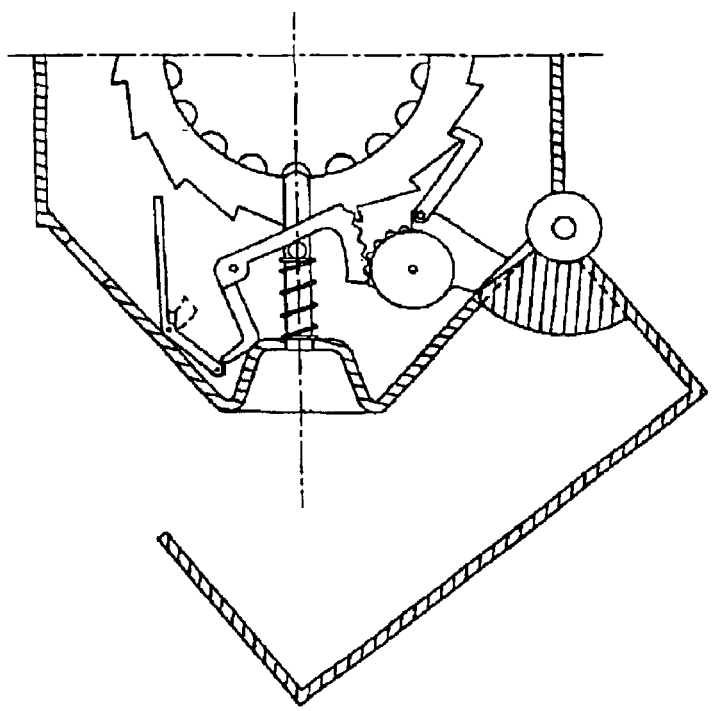
Figure 7:
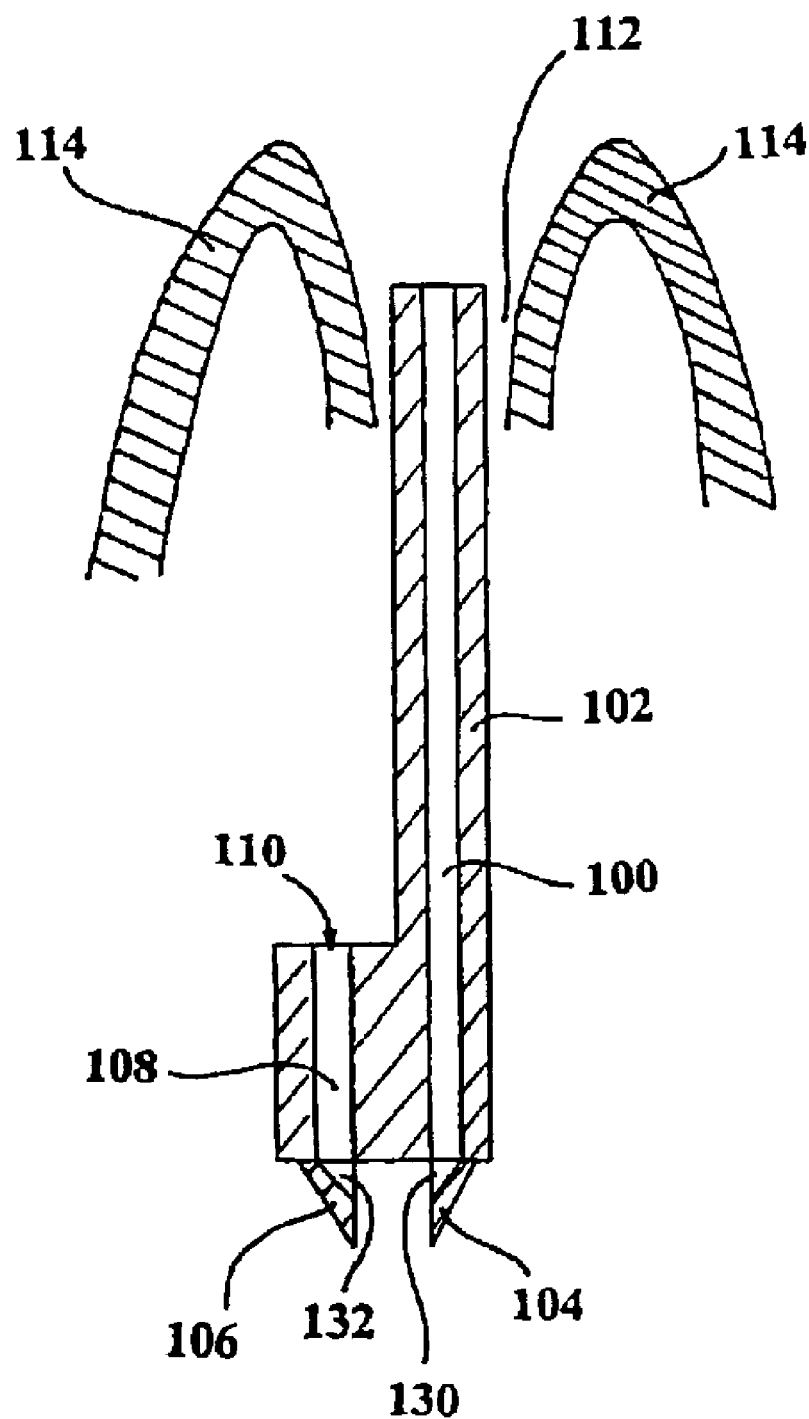
Figure 8:
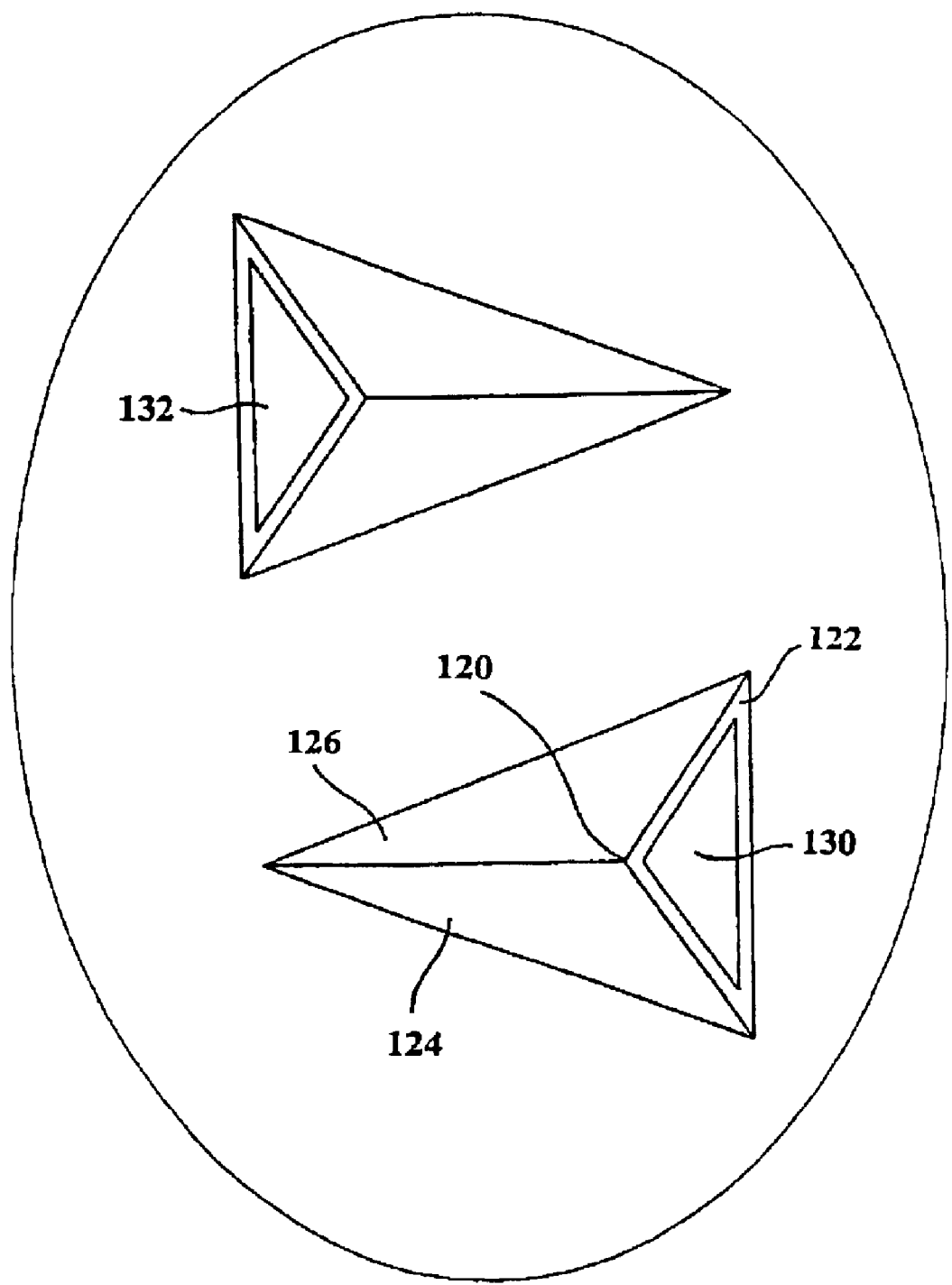
Figure 9:
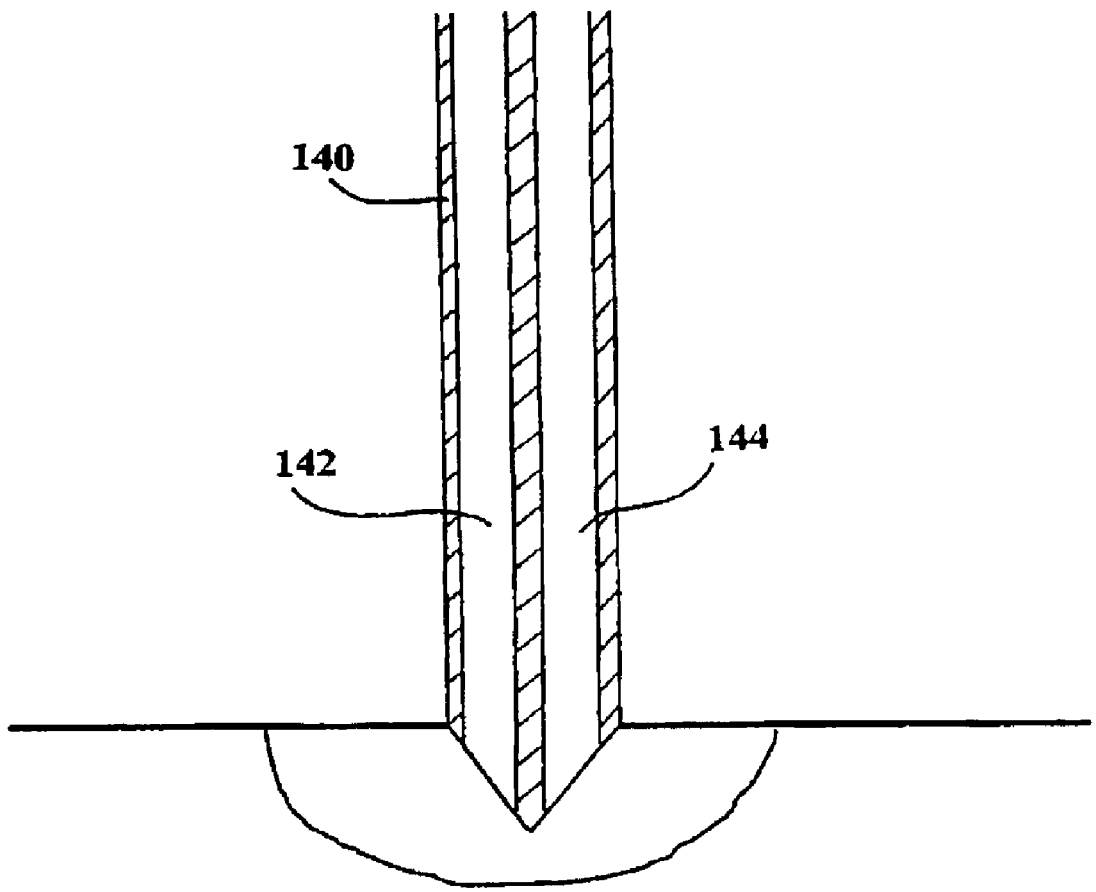
Figure 10:
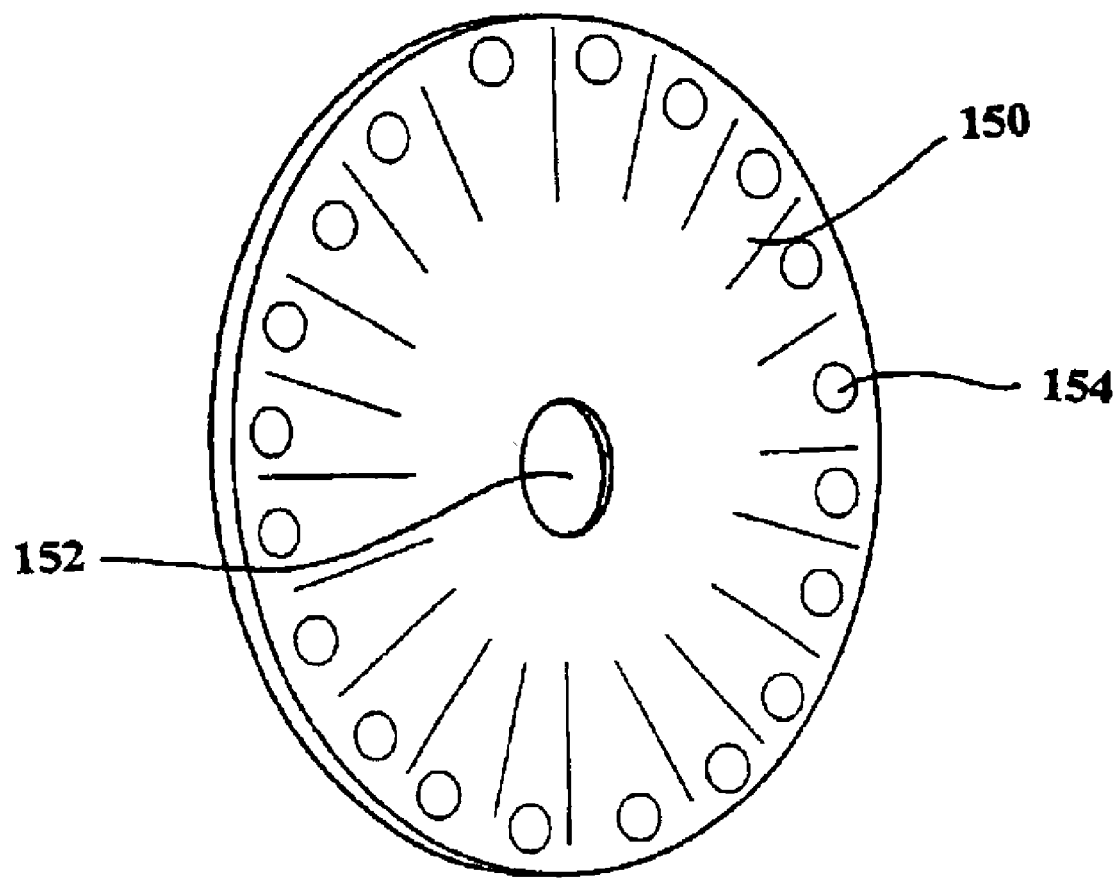
Figure 11:
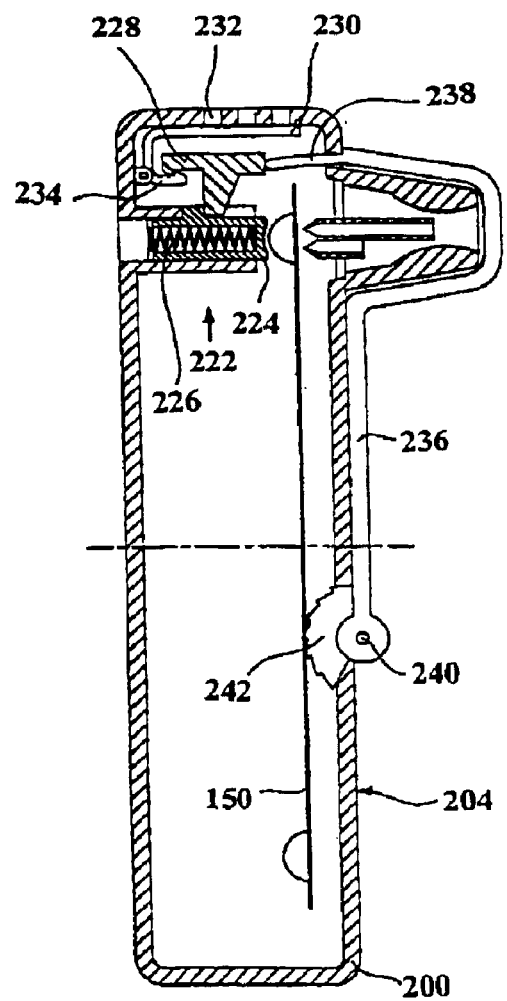
Figure 12:
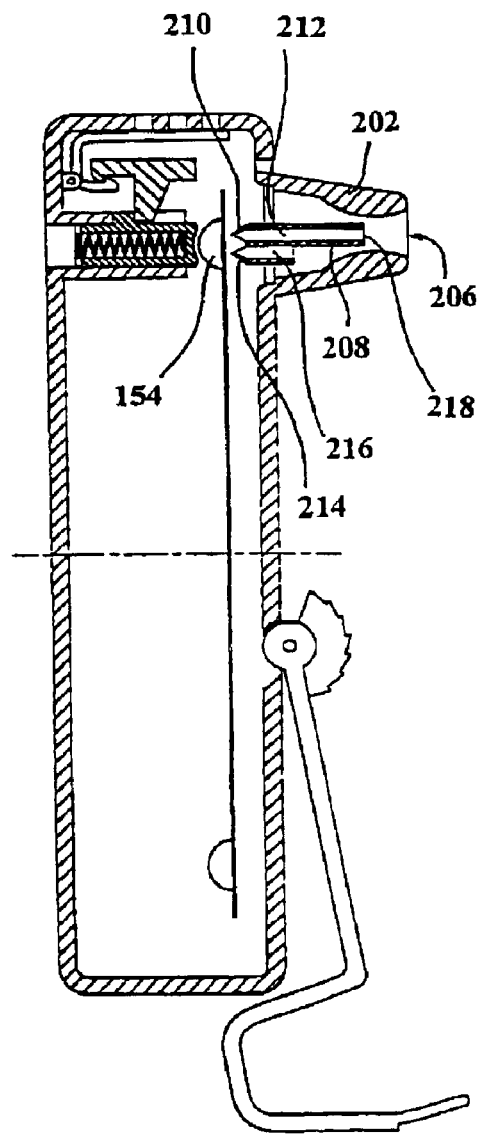
Figure 13:
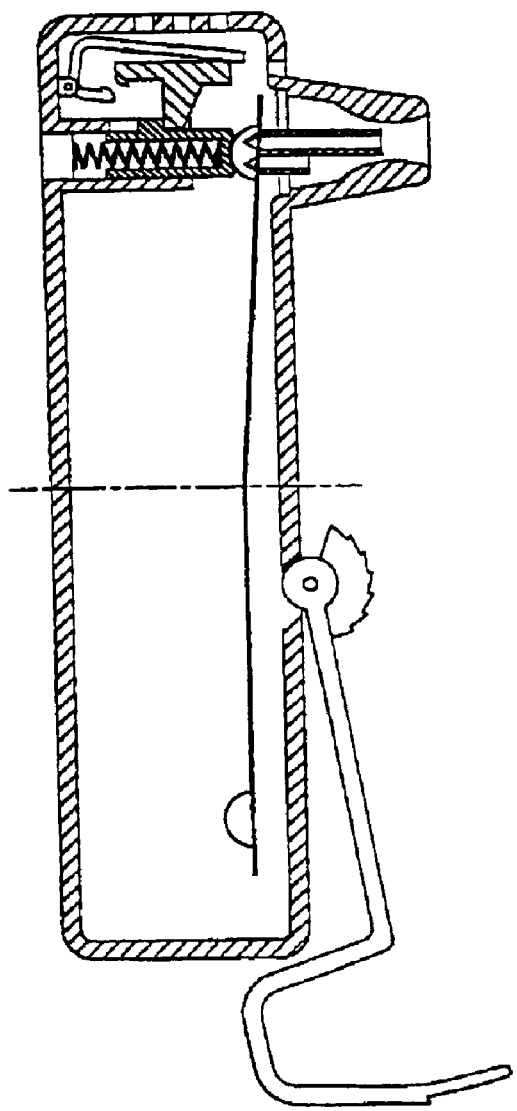
Figure 14:
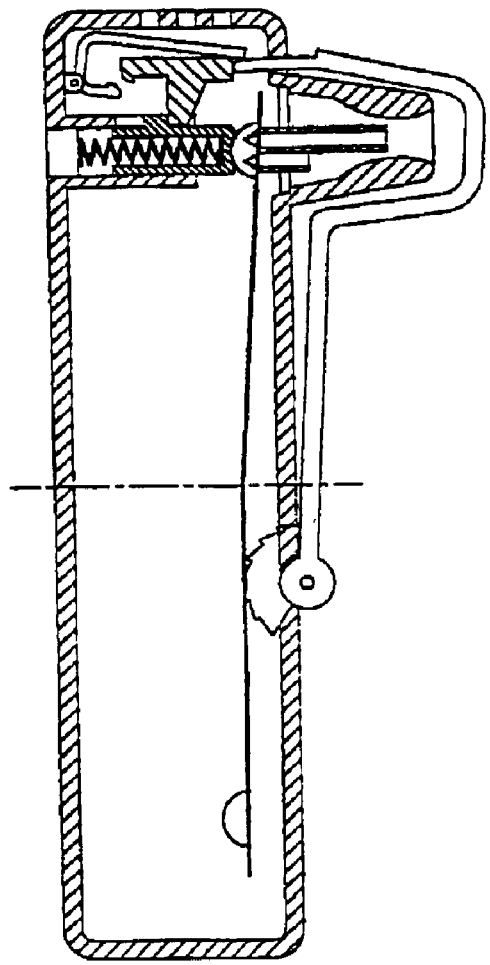
Figure 15:
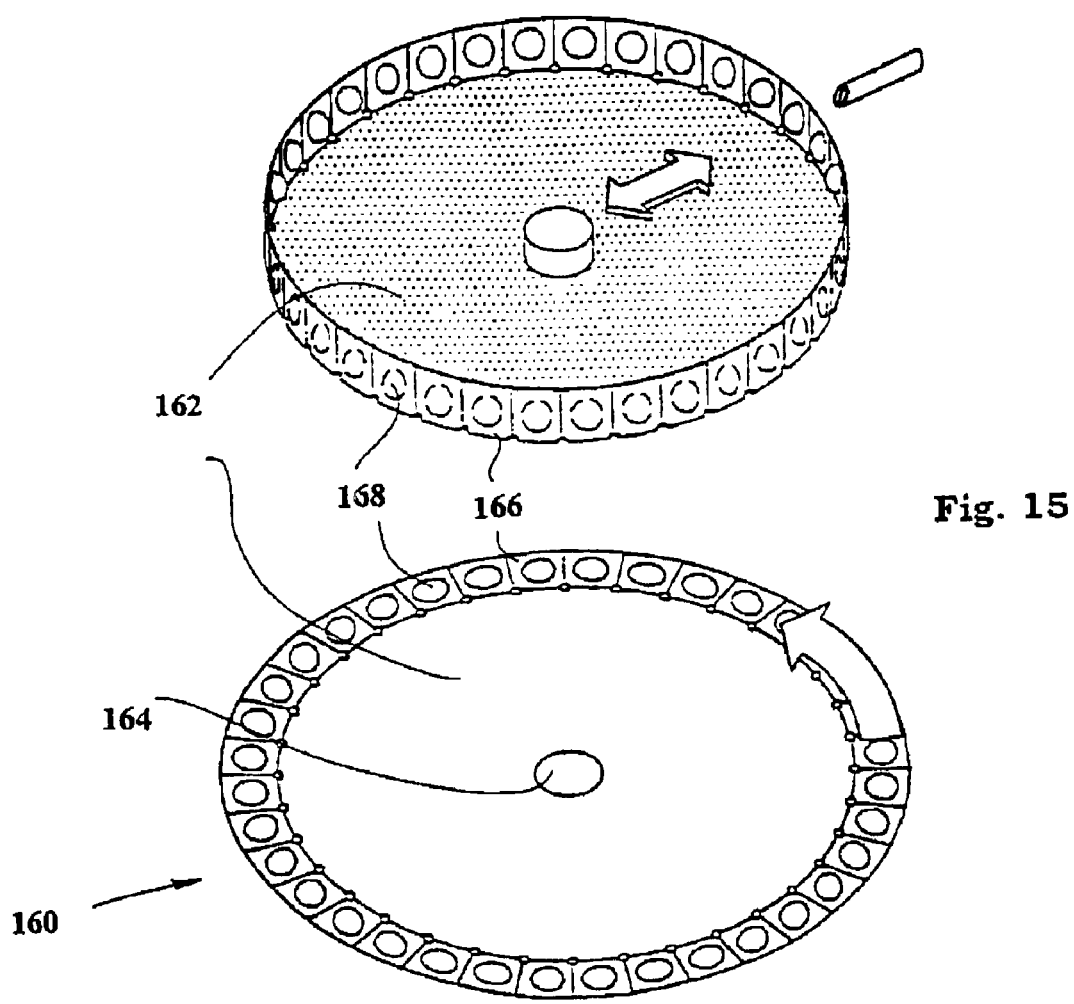
Figure 16:
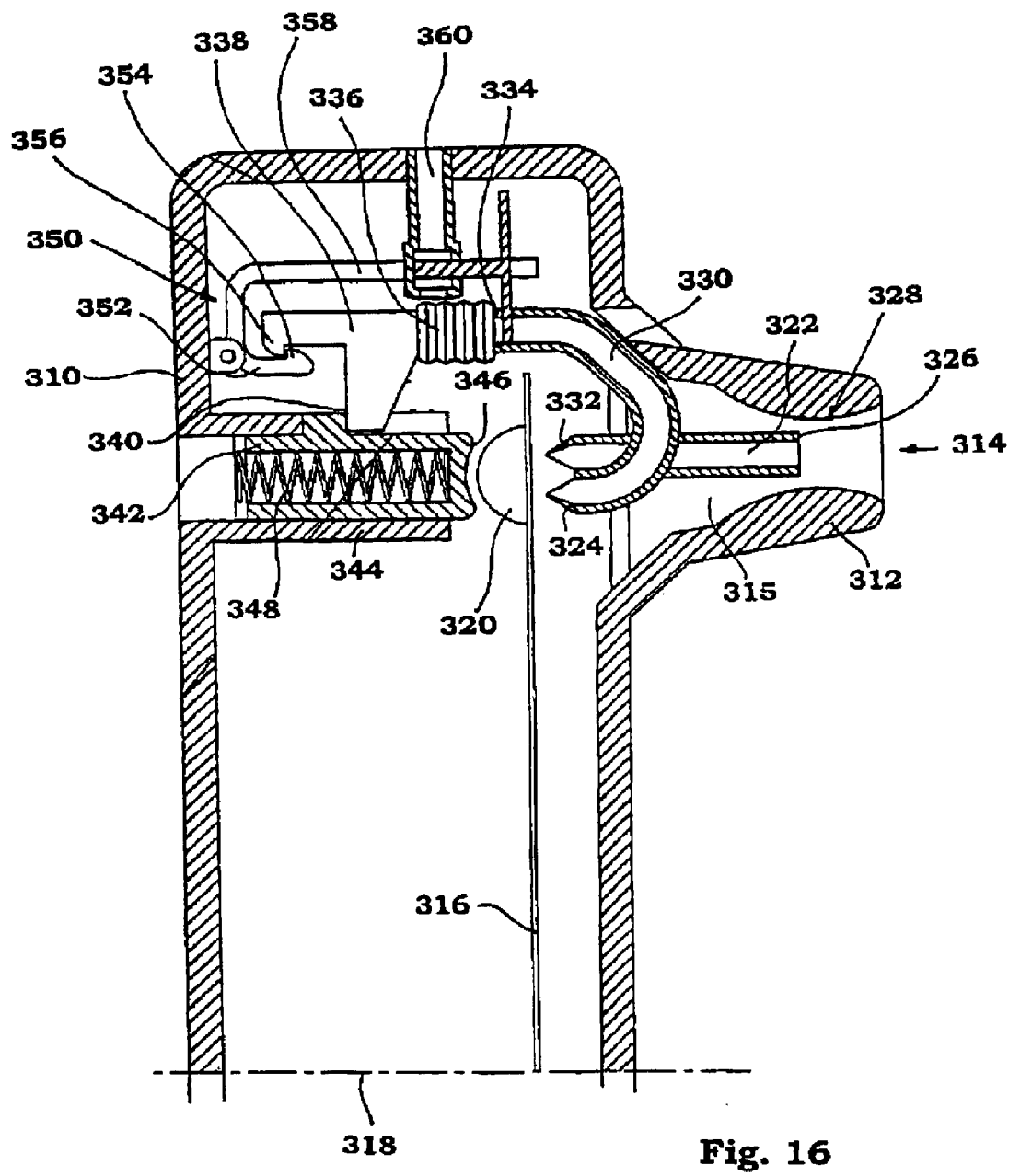
Figure 17:
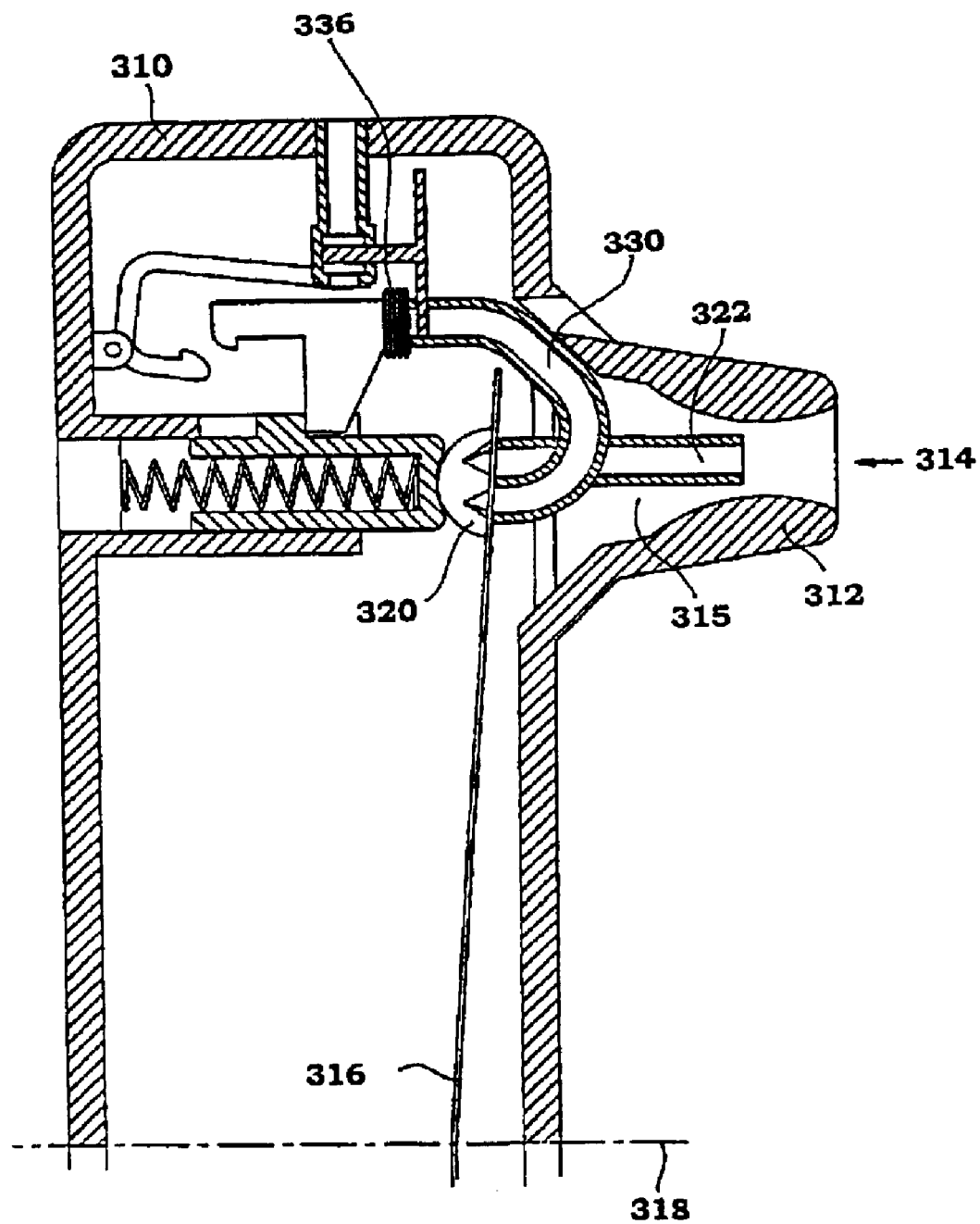
Figure 18:
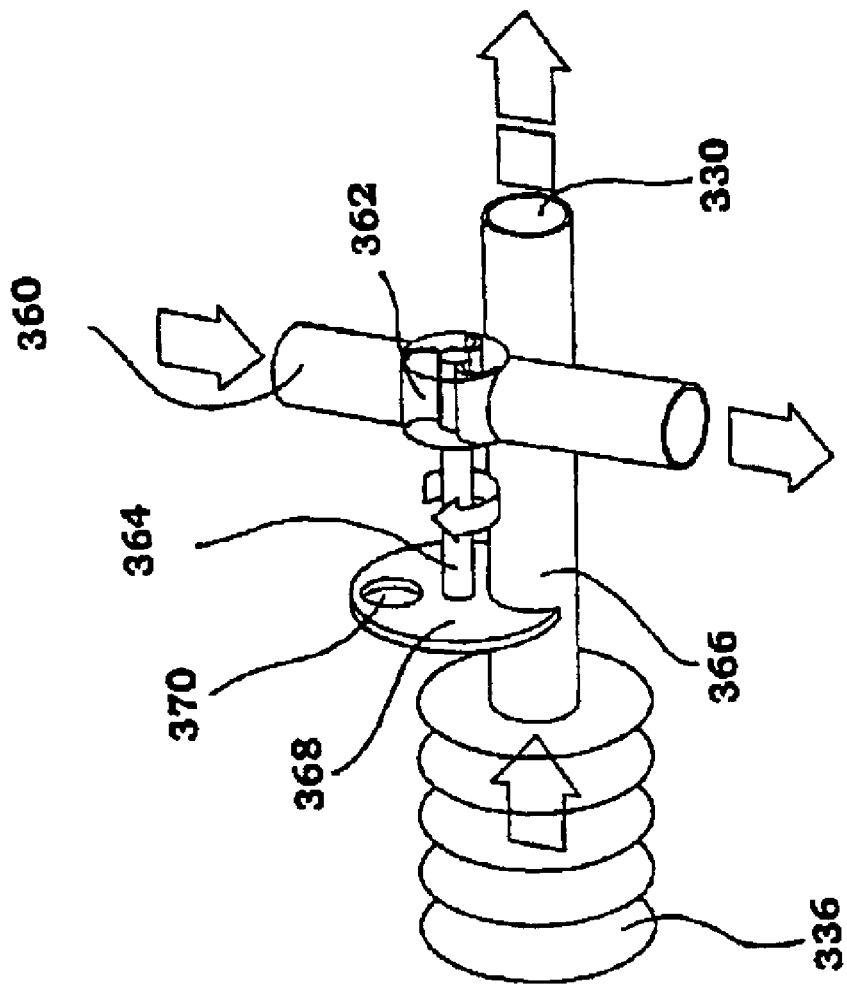

Because the air is supplied to the compartment intermittently, each "burst" of air will have an aerolising effect on the powder, thereby effectively lifting the powder and emptying the compartment. This effect also allows for controlling the medicament delivery time. There is thus no longer a need for a strong initial inhalation in order to deliver the powder effectively. Also, in connection to the distribution of the medicament in the respiratory tract according to above, this could imply that medicament could be delivered more effectively, thus providing the patient with a dose that has a better effect.

For certain types of medicament, and/or form and quantity and/or inhalation flow, it might be advantageous to "boost" the intermittent air flow into the compartment. This may be obtained by a pressure generating means such as for example a bellows, air cushion, balloon, spring loaded means, piston/cylinder means or externally arranged means, which is activated before inhalation. Another way of "boosting" the intermittent air flow is to arrange an ejector means adjacent the outlet end of the outlet passage. The air flow through the ejector and around the outlet will cause a certain ejector effect in the outlet passage thereby promoting the air flow through the compartment.

The present invention allows for a design of an inhaler that provides for possibilities to vary and control the time for aerolisation and delivery of the powder in terms of effect and time. It also allows for the design of an inhaler which allows the use of lower flows which yet provides sufficient aerolisation, and a more convenient and pleasant inhalation for the patient.

These and other aspects of, and advantages with the present invention will become apparent from the following detailed description of a preferred embodiment and by the accompanying drawings.

BRIEF DESCRIPTION OF THE DRAWINGS

In the following detailed description of a preferred embodiment, reference will be made to the drawings, of which FIG. 1 shows a perspective view of an inhaler according to the invention with a protective cover closed, FIG. 2 shows a perspective view of the inhaler of FIG. 1 with the protective cover opened, FIG. 3 shows a detailed view in cross-section of the front end of the inhaler of FIG. 1 with the protective cover closed, FIG. 4 shows the inhaler of FIG. 3 with the protective cover opened before inhalation, FIG. 5 shows the inhaler of FIG. 3 during inhalation, FIG. 6 shows the inhaler of FIG. 3 after inhalation and the protective cover being closed, FIG. 7 shows a detail view of variant of a dose access means in connection with an air ejector, FIG. 8 shows a detailed end view of the dose access means of FIG. 7, FIG. 9 shows a detailed view of a variant of a dose access enabling means according to the invention, FIG. 10 shows a variant of a blister cartridge to be used with the present invention, FIGS. 11–14 show a variant of an inhaler according to the invention with a blister cartridge according to FIG. 10, and FIG. 15 shows a variant of a blister cartridge to be used with the present invention, FIG. 16 shows a detailed view in cross-section of an inhaler comprising an embodiment of the present invention in a ready-state before inhalation, FIG. 17 shows the view of FIG. 1 after actuation of the inhaler, FIG. 18 shows an embodiment of an air supply means comprised in the present invention.

DETAILED DESCRIPTION OF THE INVENTION

The inhaler according to the drawings comprises a housing 10. At one end of the housing a mouthpiece 12 with an inhalation opening 14 is arranged. The mouthpiece is protected, when the inhaler is in the rest position, by a protective cover 16, which is pivotally attached to the housing between a rest position, FIG. 1, and an activated position, FIG. 2.

Arranged inside the opening and in the air passage is a means for enabling access to medicament 18, FIGS. 3–6. The means comprises an elongated body 20 with a passage 22 through its length, hereafter named outlet passage. One end 24, the one facing inwards, is arranged with sharpened edges. The elongated body is slidably supported in a hole in the opening, whereby the other end 26 of the elongated body is arranged in the opening. A pin 28 is arranged on the elongated body, which extends transversely to the longitudinal axis 30 of the body. A pressure spring 32 is arranged between the pin and the support wall 34 of the opening, which spring urges the elongated body inwards.

The inhaler is further provided with an activating means. It comprises a flap 38 pivotally arranged adjacent an air intake 36 and designed to be able of closing the air intake. A pressure spring 40 is arranged for urging the flap to a closing position. A lever 42 is attached to the flap extending from the opposite side of the pivoting point 44. A cantilever 46 is pivotally arranged around an axis 48, with one arm 50 in contact with the lever of the flap.

The end of the other arm 52 of the cantilever is arranged with a rack 54. The rack in turn engages a cogwheel 56 pivotally arranged around an axis. A plate 58 is attached to the cogwheel. A pawl 60 is arranged on the plate with an attachment point 62 at a distance from the pivoting point of the cogwheel. The plate is further provided with a tongue 64 extending in a direction towards the mouthpiece. In that direction an opening 66 is arranged in the mouthpiece. A protrusion 68 is arranged on the inner surface of the protective cover for interaction with the tongue through the opening in a manner, which will be described below.

Further inside the inhaler and the elongated body a wheel 70 is rotatably arranged on an axis 72, which axis is perpendicular to the longitudinal axis of the elongated body, and with the axes intersecting each other. The wheel is arranged with a plurality of recesses 74. Further the wheel is arranged with a ratchet 76 for interaction with the pawl in a manner which will be described in detail below.

The medicament is packaged in blisters 78, where each blister enclosure contains one dose of medicament. The enclosures are arranged on a strip 80 or the like elongated flexible band. The recesses of the wheel have a size and pitch so as to be able to accommodate a blister when the strip is placed around the wheel.

When loading the inhaler, the housing is opened and the strip is placed around the wheel with the blisters positioned in the recesses. A second wheel or guiding means (not shown) are arranged in the housing for guiding the strip.

The inhaler is now loaded and ready for use. When the inhaler is to be used the protective cover 16 is pivoted around its axis and the mouthpiece 14 is freed, FIG. 4.

When the inhaler is in a ready-to-use state the flap 38 covers the air intake 36 because of the pressure spring 40. Via the lever 42 and the cantilever 46 with its rack 54 engaging the cogwheel 56, the elongated body 20 is pressed in a retracted position by the cantilever acting on the pin 28 against the force of the elongated body spring 32.

Upon inhalation, air is forced through the passage 22 of the elongated body from the interior of the inhaler, creating a pressure drop there and pressure difference between the interior and outside the inhaler. The pressure difference causes the flap 38 to move around its pivot axis 44, thereby opening the air intake 36. The pivoting action of the flap causes the cantilever to pivot around its pivot axis, whereby the elongated body 20 is pushed forward by its spring force, and its front 24 end penetrating the blister cover of the blister 78 placed in the wheel in a position in the longitudinal direction of the elongated body. The front end of the elongated body is now arranged inside the blister. Because of the inhalation, the powder medicament in the blister is drawn through the passage of the elongated body and into the respiratory tract of the patient.

Due to the cantilever movement, its rack 54 rotates the cogwheel 56 in a clockwise direction in FIGS. 3 to 6, whereby the plate 58 attached to the cogwheel is also rotated. This causes the pawl 60 to be moved out of engagement with one tooth of the ratchet 76 and in contact with an adjacent tooth.

When the patient has inhaled the dose, he closes the protective cover. Upon closing the protrusion 68 on the cover comes in contact with the tongue 64 of the plate. This contact causes the plate and the cogwheel to rotate in an anti-clockwise direction in FIGS. 3 to 6.

The rotation of the cogwheel acts on the ratchet of the cantilever causing it to pivot around its axis in an anti-clockwise direction whereby the elongated body is drawn out of the blister and back against its spring force to a resting position.

The rotation causes the pawl to rotate the wheel a certain degree so that an adjacent blister is arranged in the longitudinal direction of the elongated body. In this context it is to be understood that the pitch of the recesses in the wheel and the spacing of the teeth of the ratchet correspond to each other, so that for each turning of the wheel by the pawl, an adjacent recess is placed in position.

The inhaler is now ready for the next inhalation.

With the embodiment described above it is to be understood that the interior of the inhaler has to be sufficiently sealed so that the only air flow that can occur is through the air intake closed by the flap. It is however conceivable to have some sort of air opening with reduced size, perhaps in the flap itself, in order to create some air flow when the patient inhales before the flap opens. It must however be sufficiently small in order for a pressure difference to be created over the flap.

The force of the spring acting on the flap is preferably set so that the flap opens at a certain predetermined inhalation pressure drop and air flow, considered to be a level where a proper inhalation for obtaining a sufficient dose of medicament is reached.

With the configuration according to this embodiment, rather short passage ways for air/powder are obtained, minimising the risk of powder depositing inside the inhaler, thus improving the dose to dose equivalence.

FIGS. 7 and 8 show a variant of the dose enabling means. According to FIG. 8 it comprises a first passage, outlet passage, 100 extending through the length of the elongated body 102. The end of the elongated body facing the wheel and the blisters is arranged with two pointed ends 104, 106, the shapes of which will be described in detail below. The outlet passage 100 terminates in one of the pointed ends 104. A first passage, inlet passage, 108 is arranged in the elongated body, which passage terminates in the second pointed end 106. The opposite opening 110 of the inlet passage is arranged inside the inhaler housing.

The outlet passage terminates in the air passage 112 in vicinity of the inhalation opening. In the air passage, adjacent the end of the outlet passage, guiding walls 114 are arranged and designed such that an ejector effect is obtained in that area. This ejector effect creates such an air flow through the enclosure so that an aerolization of the powder medicament is obtained and ensures a proper emptying of the enclosure. The ejector effect becomes especially important for small enclosures containing small amounts of medicament, where the small enclosures limit the size of the passages. With small passages the total air flow can not be directed through these. Therefor a major part of the air flow is directed through the air passage upon inhalation, and due to this air flow passing the end of the outlet passage in the ejector area, an ejector effect for the outlet passage is created.

As one example, the pointed ends 104, 106 of the elongated body are configured as tetrahedrons, FIG. 8, each with three triangularly shaped sides. The top point 120 of each tetrahedron is not centred, but somewhat displaced so that one of the side walls 122 has a much steeper inclination than the other two 124, 126, which have substantially the same inclination. The openings 130, 132 for the passages are arranged in the steeper side wall of the tetrahedron.

The variant with two passages works somewhat differently than the above described embodiment. There is an opening 112 arranged around the outer end of the elongated body. Upon inhalation, air is sucked through this opening, creating a pressure difference as described above, trigging the elongated body to be pushed towards the blister. When the pointed ends reach the blister cover, the edges between the side walls will cut the cover along three lines intersecting at the point 120 of the tetrahedron. When the points enter deeper into the blister, the main part of the cut-up cover will roll or curl up against the side walls 124, 126 with lesser inclination and form a certain seal to prevent powder inside the blister to escape, and a small part will be in contact with the side wall 122 with the steeper inclination. Because of this, the opening is provided in the side wall with steeper inclination to reduce the risk of cut cover material blocking the opening. With this configuration, the cutting open of the blister is controlled in a very efficient and safe way, as regards, sealing of the blister and preventing cover material from being cut off.

When the pointed ends are inside the blister, the two passages form an air passage through the blister. During inhalation, the ejector arranged around the opposite end of the passage will create an air flow from the interior of the inhaler through the inlet passage into the blister and out through the outlet passage and further through the inhalation opening. Due to position of the two pointed ends, FIG. 8, where the openings are directed in opposite direction, a swirling movement of the air inside the blister is created, which improves the emptying of the medicament in the blister.

In this respect it is to be noted that the shape of the blister itself may enhance the swirling effect. It is also conceivable to arrange the pointed ends in other directions and arrange so that they can be oriented independently.

In FIG. 7 the means for enabling access is designed as one single unit. It is of course conceivable to have two separate unites, each with one pointed end and passage. In this respect it is also conceivable to have one point protruding a distance further than the other, preferably the outlet passage. If the outlet passage enters the blister enclosure first, a negative pressure is built up in the blister due to the inhalation before the inlet passage creates the flow of air through the blister. The negative pressure aid in preventing powder from escaping the blister during penetration of the points.

It is to be understood that the pointed ends may have other forms for enabling access in a controlled way. For instance the ends may have more than three triangular sides, that the intersections between the sides are provided with sharp protruding edges or that all sides have the same inclination.

FIG. 9 shows a variant with one elongated body 140 provided with two passages 142, 144, one inlet and one outlet passage with openings at the same distance from the end point or with some difference in distance to obtain the function described above.

FIG. 10 shows a variant of the blister cartridge 150 where the main body is a disc with a centre 152 enabling rotation of the disc. The blisters 154 are arranged on a circle at a distance from the centre.

FIGS. 11 to 14 show a variant of the inhaler according to the invention. With this variant, in order to obtain short air/powder passages, the inhalation opening is placed rather on the side of the inhaler than at the end as with the first embodiment. The inhaler comprises a housing 200 arranged with a mouthpiece 202 at the upper end of a side surface 204 of the inhaler. In the inhalation opening 206 of the mouthpiece, an elongated body 208 provided with a pointed end 210 and a passage 212, hereafter named outlet passage, is fixedly arranged. The elongated body is arranged with a second pointed end 214 and a second passage 216, hereafter named inlet passage. The inhalation opening adjacent the outlet end 218 is arranged with a shape providing an ejector effect. A blister cartridge 150 according to FIG. 10 is arranged rotatably around an axis 220, which is parallel with the longitudinal direction of the elongated body and at a distance thereof so that the circle 156 along which the blister enclosures 154 are placed intersect with the longitudinal direction of the elongated body.

On the opposite side of the blister cartridge in relation to the elongated body, and also in the longitudinal direction of the elongated body, an activating means 222 is arranged. It comprises a pressure member 224 slidably arranged in a holder. A pressure spring 226 is arranged between the pressure member and the housing, which pressure spring urges the pressure member towards the blister cartridge. A holding member 228: is in contact with said pressure member. A flap 230 is pivotally arranged adjacent an air intake 232 in the inhaler housing. At the opposite side of the pivoting point, the flap is arranged with an arm 234, where the end of the arm is arranged with a ledge, engaging a corresponding ledge in the holding member. A protective cover 236 is pivotally arranged to the inhaler housing comprising a tongue 238, which, when the protective cover is closed, FIG. 11, extends through a passage in the housing and in contact with the holding member. Adjacent its pivoting point 240, the protective cover is arranged with feed means, comprising a toothed wheel 242 engaging the surface of the blister cartridge.

The function is as follows. When the protective cover 236 is pivoted away from the mouth piece 202, i e when a patient is to inhale a dose of medicament, the tongue securing the holding member 228 is removed and the inhaler is ready for use, FIG. 2. Upon inhalation, a pressure difference between the interior and the exterior of the inhaler is created. The pressure difference will cause the flap 230 to pivot, thereby opening the air intake 232 so that an air flow is created. The pivoting action of the flap will cause the ledge of the arm 234 to move out of contact with the ledge of the holding member. Because the holding member is in contact with the pressure member 224, the pressure member will be urged forwards by the force of the pressure spring 226.

In turn the pressure member will push the blister enclosure 154 against the pointed ends 210, 214 of the elongated body 208, FIG. 3. The pointed ends will penetrate the enclosure and be positioned inside the enclosure due to the pressure from the pressure member. The inlet passage and the outlet passage of the elongated body have created a flow path so that during the inhalation, due to the ejector effect, air is drawn into the enclosure via the inlet passage, in which enclosure the air is mixed with the medicament and the mix is drawn through the outlet passage and into the respiratory tract of the patient.

When the patient has received the dose, the protective cover is closed. The pivoting movement of the protective cover causes a rotational movement of the feed wheel 242 so that the blister cartridge is rotated and a subsequent blister enclosure is placed before the elongated body. The closing of the protective cover causes the tongue to engage the holding means, FIG. 4, and to push it and the pressure means until the ledges of the arm and the holding means engage. The inhaler is now ready for a subsequent dose delivery.

FIG. 15 shows another variant of the blister cartridge 160 to be used in an inhaler with a similar design to the one described in the first embodiment, where the main body is a disc 162 with a centre 164 enabling rotation of the disc. A number of tongues 166 are arranged at the circumference of the disc, on which tongues blisters enclosures 168 are arranged. When, or before, placing the disc in the inhaler, the tongues are folded upwards or downwards.

Although blisters have been used to exemplify the present invention, it is to be understood that other enclosures containing specific doses of medicament may be utilised, and also other means for positioning the enclosures in relation to the dose enabling means. These may include capsules and the like placed in magazines such as revolver magazines.

With an inhaler according to the invention it is possible to have certain parts exchangeable in order to obtain a high degree of hygiene and to prevent any eventual collections of powder in the inhaler to reach such amounts over long periods of use so that they may loosen and cause overdoses. These parts may include the mouthpiece, the elongated body or bodies and other that may be considered to be replaced frequently.

Although the elongated bodies have been shown to be movable in order to enable access to the medicament, it is to be understood that the elongated body can be fixed and that the medicament enclosures are movable to and from the elongated body in order to achieve the same function.

For certain types of medicament, especially medicament formed as larger agglomerates that need to be reduced in size by breaking or pulverising before entering the respiratory tract, the inhaler may be provided with swirling means to cause a turbulence of the air flow containing medicament so that the medicament is reduced in size during interaction with the inhaler.

A further embodiment of the inhaler according to the invention is shown in FIGS. 16 to 18. It comprises a housing 310 arranged with a mouthpiece 312 arranged with an inhalation opening 314. The inhalation opening is connected to an inhalation passage 315, hereafter named outer passage, which extends into the interior of the inhaler. Inside the housing a circular disc 316 is arranged rotatably around an axis 318. Adjacent the: periphery of the disc a plurality of compartments 320 are arranged. Each compartment contains a metered dose of powder, whereby the powder is sealed off from the environment and thus protected against moist and the like. A first air passage 322, hereafter named outlet passage, is arranged between the inhalation opening and the disc. The end 324 of the outlet passage facing the disc is provided with a pointed end. The other end 326 of the outlet passage is arranged in the outer passage 315 where the outer passage in the mouthpiece is provided with an air balancing means 328 which narrows around the outlet passage, thus reducing the cross-sectional area of the outer passage. This configuration causes an air balancing effect, which will be described in detail later.

A second air passage 330, hereafter named inlet passage is attached to the outlet passage. One end 332 of the inlet passage is arranged adjacent the end of the outlet passage facing the disc, whereby this end of the inlet passage also faces the disc. This end is also provided with a pointed end. The other end 334 of the inlet passage is attached to a pressure generating means 336, in the embodiment shown a bellows. The opposite side of the bellows is attached to an actuating member 338, which is movable to and from the bellows. The bellows is further provided with a one-way valve (not shown) for allowing air into the bellows. The actuating member is arranged with a ledge 340. The ledge is in contact with a pressure member 342 in the form of a cylindrical sleeve slidably arranged in a cylindrical guide 344. The end of the pressure member is arranged with a counterstay 346 facing the disc and is arranged such that the counterstay is in line with the pointed ends of the passages. A pressure spring 348 is acting on the pressure member urging it towards the disc and the pointed ends.

A lever 350 is pivotably arranged to the inside of the housing. One arm 352 of the lever is arranged with a hook 354, which engages a corresponding hook 356 of the actuating member. The other arm 358 of the lever is formed as a flap or vane and arranged adjacent, and covering, an air intake in the housing. A further air intake 360 is arranged in the housing, comprising a cylindrical tube. In the tube an air turbine 362 is fixedly attached to a rotatable shaft 364, FIG. 18. The shaft is arranged adjacent a section 366 of the inlet passage with its rotational axis parallel with this section of the inlet passage. On the shaft a disc 368 if fixedly attached, which disc is arranged, and with a size, such that it is able to rotate in a slot in the section of the inlet passage and covering the majority of the cross-section of the inlet passage. The disc is arranged with a through-hole 370 with a diameter adapted to provide suitable air passages.

The function is as follows. When the inhaler is activated and in a ready-state, FIG. 16, the actuating member 338 is drawn back, to the left in FIG. 16, by a manual means (not shown) like a protective cover, a lever or the like. When the actuating member is drawn back, the bellows 336 is expanded whereby air is drawn into the bellows via the one-way valve. The pressure member 342 is also drawn back because of the contact between the actuating member and the pressure member, whereby the pressure spring 348 is compressed. The actuating member is held in place by the hook 354 of the lever 350.

When a patient begins to inhale a pressure difference is created between the interior and the exterior of the inhaler due to the suction in the inhalation opening 314. This pressure difference causes the flap or vane 358 to move from the air intake and the lever 350 to pivot and the hook to release the actuating member 338. The pressure spring 348 will then push the pressure member towards the disc whereby the counterstay 346 pushes the compartment 320 containing powder against the pointed ends 324, 332 of the passages. These will then penetrate the compartment wall and create an inlet passage to, and outlet passage from, the compartment. At the same time the pressure spring will act on the bellows 336 compressing it and the air entrained inside the bellows. The air flow caused by inhalation will also flow through the air intake tube 360 and cause the turbine 362 to rotate and thereby the disc 368. The pressurised air from the bellows will try to escape through the inlet passage 330 but is prevented until the through-hole 370 of the rotating disc is aligned with the inlet passage. Each time this occurs a certain amount of pressurised air will flow through the inlet passage 330 and into the compartment 320, aerolising the powder, and flow through the outlet passage 322 and into the lungs of the patient. If the inhaler is designed for rather large air flows, the inhalation flow in the outer passage 315 and through the air balancing means 328 and around the outlet passage will cause a certain ejector effect and assist the air flow in the outlet passage.

If the inhaler is designed for smaller air flows, the air balancing means will act as a kind of throttle and limit the air flow around the outlet passage so that a larger air flow is directed through the outlet passage. In this way the amount of inhalation air in the outlet passage may be balanced or controlled by increasing or decreasing the cross-sectional area of the outer passage. For certain applications and desired air flows the outer passage may be omitted completely, thus directing the entire air flow through the outlet passage.

In this context it is to be noted that the inhaler may be provided with further de-agglomerating means such as whirl chambers, impellers and hairline crosses.

Even though the present invention has been described in connection with a powder inhaler with individually enclosed doses of medicament, it is to be understood that the principles of the present invention may be employed with other types of inhalers where a dose of powder is taken from a larger compartment and is placed in a compartment ready for delivery.

What is claimed is:

1. Inhaler for medicament in powder form with an opening (14) intended for inhalation; said powder medicament is arranged in the inhaler in a number of enclosures (78, 154, 168), where each enclosure comprises a specific dose of medicament, means (46) for enabling access to said dose of medicament, wherein said means for enabling access arranged and designed such that it is able to be inserted inside said enclosure and establish at least one outlet passage (22, 100), between an interior of said enclosure and an inhalation opening, through which outlet passage the medicament is delivered to the patient upon inhalation characterised in breath-activated activating means connected to said means for enabling access, wherein said breath activated activating means, and said means for enabling access, are activated when the pressure drop/air flow in an air passage in said inhaler reaches a certain threshold value.

2. Inhaler according to claim 1, characterised in that said means for enabling access comprises a flap (38) movably arranged in said air passage and spring means (32), wherein, upon inhalation, said flap moves and activates said spring means, which in turn establishes said outlet passage.

3. Inhaler according to claim 1, characterised in that said means for enabling access further comprises an inlet passage (108), which inlet passage, upon inhalation, acts as an air supply to the enclosure.

4. Inhaler according to claim 3, characterised in that said means for enabling access comprises at least two elongated bodies with cutting means, which cutting means cut through a wall of said enclosure, wherein one of said at least two elongated bodies comprises said at least one outlet passage and the other of said at least two elongated bodies comprises said at least one inlet passage.

5. Inhaler according to claim 1, characterised in that said means for enabling access comprises an elongated body (20,102) with a cutting means (24,120), which cutting means penetrates a wall of said enclosure in a controlled manner.

6. Inhaler according to claim 5, characterised in that said cutting means has a shape in the form of a plurality of side walls, where each side wall has the shape of a triangle, that one corner of each triangle together form a pointed end, that the edges of adjacent triangles act as cutters when breaking through an enclosure wall, and that an opening (130,132) of the passage inlet and outlet passages is arranged in at least one of the side walls (122).

7. Inhaler according to claim 6, characterised in that, when two cutting means are used, the openings (130, 132) are arranged facing different directions in order to create a swirling movement of air/powder inside the enclosure during inhalation.

8. Inhaler according to claim 1, characterised in that the air passage is arranged with an air ejector (112,114), which, upon inhalation, generates the air flow through said dose enclosure.

9. Inhaler according to claim 1, characterised in an air supply means (336, 368, 370) capable of, during inhalation, to supply air intermittently via the inlet passage (330) to a compartment (320) within said inhaler.

10. Inhaler according to claim 9, characterised in that the air supply means is designed and arranged such that it intermittently opens and closes either the inlet passage (330) or the outlet passage (322).

11. Inhaler according to claim 9, characterised in that the air supply means is capable of generating and supplying air with a positive pressure.

12. Inhaler according to claim 9, characterised in that the inhaler is arranged with an outer air passage (315), connected to the inhalation opening, in that an outlet end of the outlet passage is arranged in the outer passage, and adjacent the outlet end, the inhalation opening is arranged with inhalation air balancing means (328).

13. Inhaler according to claim 12, characterized in that, for higher air flows, the air balancing means provides an ejector effect to the air flow through the outlet passage during inhalation.

14. Inhaler according to claim 12, characterized in that, for lower air flows, the air balancing means providing a throttle effect on the air flow through the outer passage during inhalation.

* * * * *